(12) United States Patent
Cyncynatus et al.

(10) Patent No.: US 8,088,592 B2
(45) Date of Patent: Jan. 3, 2012

(54) **USE OF THE 7F4 PROTEIN IN THE IN VITRO DIAGNOSIS OF *MYCOPLASMA PNEUMONIAE* INFECTIONS**

(75) Inventors: Camille Cyncynatus, Saint Maurice (FR); Helene Nuyttens, Paris (FR)

(73) Assignees: Ingen Biosciences, Chilly Mazarin (FR); Universite Victor Segalen Bordeaux 2, Bordeaux (FR)

( * ) Notice: Subject to any disclaimer, the term of this patent is extended or adjusted under 35 U.S.C. 154(b) by 0 days.

(21) Appl. No.: 12/444,281

(22) PCT Filed: Oct. 3, 2007

(86) PCT No.: PCT/FR2007/001618
§ 371 (c)(1),
(2), (4) Date: Jun. 5, 2009

(87) PCT Pub. No.: WO2008/040883
PCT Pub. Date: Apr. 10, 2008

(65) Prior Publication Data
US 2010/0136040 A1    Jun. 3, 2010

(30) Foreign Application Priority Data
Oct. 5, 2006  (FR) ..................... 06 08734

(51) Int. Cl.
*G01N 33/554* (2006.01)
(52) U.S. Cl. ............ 435/7.32; 435/4; 435/7.2; 435/7.92
(58) Field of Classification Search ........................ None
See application file for complete search history.

(56) References Cited

U.S. PATENT DOCUMENTS
5,788,962 A    8/1998 Wise et al.

FOREIGN PATENT DOCUMENTS
EP      0 475 185     3/1992
EP      1 098 001     5/2001
WO      96/28472      9/1996

OTHER PUBLICATIONS

Hilbert et al (Nuc.Acid Res. 1996. 24: 628-639).*
Himmelreich et al (Nuc. Acid Res., 1996. 24: 4420-4449).*
Greenspan et al (Nature Biotechnology 7: 936-937, 1999).*
Chothia et al (The EMBO Journal, 1986, 5/4:823-26).*
Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Dan Zilberstein et al., "The B-Subunit of the F1F0-ATPase Is Conserved in Mycoplasmas", The Journal of Biological Chemistry, Jun. 5, 1986, pp. 7109-7111, vol. 261, No. 16.
Karen E. Sjostrom et al., "Distinctive Antigenic Specificities of Adenosine Triphosphatases and Reduced Nicotinamide Adenine Dinucleotide Dehydrogenases as Means for Classification of the Order Mycoplasmatales", International Journal of Systematic Bacteriology, Apr. 1983, pp. 218-228, vol. 33, No. 2, International Union of Microbiological Societies.
"ATP synthase subunit beta (EC 3.6.3.14) (ATPase subunit beta) (ATP synthase F1 sector subunit beta)", Database UniProt, Nov. 1, 1997, Retrieved from EBI accession No. UNIPROT:Q50331.
Takashi Shimizu et al., "A Dipalmitoylated Lipoprotein from *Mycoplasma pneumoniae* Activates NF-kB through TLR1, TLR2, and TLR6", The Journal of Immunology, 2005, pp. 4641-4646, vol. 175, No. 7, The American Association of Immunologists, Inc.
Tsuguo Sasaki et al., "Cross-Reactive Antibodies to *Mycoplasmas* Found in Human Sera by the Enzyme-Linked Immunosorbent Assay (ELISA)", Microbiology and Immunology, 1987, pp. 521-530, vol. 31, No. 6.

* cited by examiner

*Primary Examiner* — Jennifer Graser
(74) *Attorney, Agent, or Firm* — Young & Thompson

(57) ABSTRACT

A method for determining if an individual is infected by *Mycoplasma pneumonia*, including, determining if antibodies directed against a protein comprising SEQ ID NO: 2 are present in a biological sample of the individual, and deducing therefrom that the individual is infected by *Mycoplasma pneumoniae*.

4 Claims, No Drawings

USE OF THE 7F4 PROTEIN IN THE IN VITRO DIAGNOSIS OF *MYCOPLASMA PNEUMONIAE* INFECTIONS

The present invention relates to the use of a polypeptide and of a polynucleotide in the field of the serological diagnosis of *Mycoplasma pneumoniae* infections.

*Mycoplasma pneumoniae* is a bacterium which grows intra-cellularly and does not have a wall and which invades the respiratory epithelial cells. It is responsible for acute respiratory infections which are frequently encountered in children aged 5 and above and in young adults. These infections can be atypical pneumonias with favorable evolution sometimes associated with other ORL, cutaneous, hematological, neurological manifestations, or more frequently tracheobronchitises. *Mycoplasma pneumoniae* is said to be responsible for 15 to 20% of the community pneumopathies which manifest themselves in the endemic state with small epidemic upsurges every four to seven years (Bébéar C, Bébéar C. M and de Barbeyrac B. in Freney J, Renaud F, Hansen W, Bollet C, Précis de bactériologie clinique, ed. ESKA, Paris, 2000).

There is a first peak of incidence in children aged from 5 to 15 years, in whom *Mycoplasma pneumoniae* is said to be responsible for almost 40% of cases of community pneumonia, of which almost 20% require hospitalization. The second peak of incidence concerns adults after age 50, with figures that increase gradually with age until they exceed 30% (Brunner H, *Mycoplasma pneumoniae* infections. Isr. J. Med Sci. (1981), 17:516-523; Ghosh et al. Surveillance of *Mycoplasma pneumoniae* infections in Scotland 1986-1991. J. Infect. (1992), 25: 221-227; Waites et al. *Mycoplasma pneumoniae* and its role as a human pathogen. Clin. Microbiol. Rev. (2004), 17: 697-728). The considerable delay between primo-infection in the child and reinfection in the adult shows that infection in the child confers on the individual effective immune protection against reinfection.

A clinical association between *M. pneumoniae* and asthma in children has also been observed, although the nature of the correlation has not yet been clearly established (Hansbro P M et al., Role of atypical bacterial infection of the lung in predisposition/protection of asthma. Pharmacology et Therapeutics (2004), 101: 193-210).

It would appear that acute, and even chronic, *M. pneumoniae* infections in children are frequently underestimated through pathologies such as asthma or community pneumopathies.

*Mycoplasma pneumoniae* enters the organism by the aerial route (inhalation of droplets, direct contact with infected subjects) by adhering to the cells of the respiratory epithelium. This contact causes oxidative stress, which results in alteration of the ciliary movement and the formation of cell lesions. A local inflammatory reaction is produced. The immunological reaction can lead to the appearance of infiltrates and sometimes even of autoantibodies. Some *M. pneumoniae* membrane antigens are in fact similar to antigens found in the brain and the pancreas (Waites K B, Talkington D F. *Mycoplasma pneumoniae* and its role as a human pathogen, Clin Microbiol Rev, 2004).

Many infectious agents, both viral and bacterial, can be at the origin of a pneumonia and the respiratory symptomatology scarcely makes it possible to distinguish *M. pneumoniae* infections from those caused by other atypical pneumonia agents. The start of the disease is progressive after incubation of 15 to 20 days. The disease manifests itself in fever, discomfort, headaches, myalgias and rachialgias and, especially, a dry and persistent cough. The general condition is scarcely altered and the physical examination shows few symptoms, contrasting with the importance of radiological images of the lungs. The disease is generally regressive with time, but convalescence is long and the cough is persistent. *M. pneumoniae* can also cause various extrapulmonary complications by dispersing to other organs: pleurisy, cutaneous eruptions, sinusitis, myocarditis, pericarditis, articular attacks, hemolytic anaemia, nervous manifestations, genital infections (Waites K B, Talkington D F. *Mycoplasma pneumoniae* and its role as a human pathogen, Clin Microbiol Rev, 2004).

The treatment of *Mycoplasma pneumoniae* infections is based on a probabilistic choice according to age, especially in children, and clinical and radiological criteria, none of which is either very specific or sensitive.

The absence of a wall makes this bacterium insensitive to penicillin and other beta-lactamines that are conventionally prescribed in cases of pneumonia of bacterial origin. Accordingly, the antibiotics frequently used in *M. pneumoniae* infections are tetracyclines, fluoroquinolones, macrolides and related compounds. However, it has already been possible to observe cases of fluoroquinolone and macrolide resistance (Matsuoka et al. Characterization and Molecular analysis of Macrolide-Resistant *Mycoplasma pneumoniae* clinical isolates obtained in Japan. Antimicrob Agents Chemother, 2004, 48, 12: 4624-4630; Gruson D. et al. In vitro development of resistance to six and four fluoroquinolones in *Mycoplasma pneumoniae* and *Mycoplasma hominis* respectively. Antimicrob Agents Chemother, 2005, 49, 3: 1190-1193). These resistance problems make the diagnosis of *M. pneumoniae* essential so that the antibiotic therapy is appropriate and is administered early.

At present, direct diagnosis is made by culturing or polymerization chain reaction (PCR); as for indirect diagnosis, there are serological tests, such as cold agglutinins, the complement fixation reaction, indirect immunofluorescence, passive agglutination and ELISA tests. However, there is no reference diagnostic test for detecting *M. pneumoniae* infections.

The culture of *M. pneumoniae* can be carried out from throat samples, from nasopharyngeal aspirations in children and from bronchoalveolar washings, but it takes a long time (from 2 to 3 weeks) and is laborious. Rarely carried out routinely, it tends to be reserved for reference laboratories. However, when it is positive, it is 100% specific. Because the bacterium can persist for up to several weeks after infection, complementary tests, such as the assay of specific antibodies, are necessary in order to confirm the diagnosis of an active infection.

Gene amplification by PCR, starting from samples from the respiratory tract, is a more rapid and more sensitive method than culture (of 100 samples which were positive by PCR, only 60 are positive by culture). Various systems have been proposed, amplification of sequences at random, amplification of the adhesin gene or of the gene coding for RNA 16S. This approach is sensitive (from 78 to 92%), permitting the detection of from 10 to 100 cfu with good specificity (from 92 to 100%) (Loens K, Goossens H and Leven M., Molecular Diagnosis of *Mycoplasma pneumoniae* respiratory tract infections, J. Clin. Microbiol., 2003). However, there is no commercially available detection kit, the technique therefore not being standardized and remaining very costly and too complex to use routinely in the majority of clinical microbiology laboratories.

Serologies are the methods most often used in diagnozing *M. pneumoniae* infection, especially where there are no samples. Following a *M. pneumoniae* infection, the immune system of a non-immunodeprived individual responds quickly by producing antibodies, which reach a peak after 3 to 6 weeks and subsequently decline gradually over a period ranging from several months to several years. The production of immunoglobulins M (IgM) specific for *M. pneumoniae* occurs 7 to 10 days after the start of the infection. Their detection is often proof of a recent infection, especially in young children who have not been repeatedly exposed to the bacterium. However, in adults who have been repeatedly exposed, *M. pneumoniae* infection does not cause a rapid increase in IgM and, in that case, commercial serological tests that detect an IgM response may be incorrect. Likewise, because the IgM response can last for months or even years, the level of IgM antibodies does not necessarily reflect a recent infection. In some cases, reinfection leads to an increase in the level of IgG, and for that reason it is recommended to look for an IgG and an IgM response in parallel. IgAs are produced early on in the infection, but their level of production decreases more rapidly than that of IgGs and IgMs. They can be good indicators of a recent infection for all age groups, even after multiple reinfections (Waites K. B., C. M. Bébéar, J. A. Robertson, D. F. Talkington and G. E. Kenny. Laboratory diagnosis of mycoplasmal infections. Cumitech of American Society for Microbiology, coordinating editor: F. S. Nolte, 2001, ASM press: 1-30).

There are various serological techniques, which are often complementary, for diagnozing an *M. pneumoniae* infection. The main tests are the detection of cold agglutinins, the complement fixation reaction, indirect immunofluorescence, passive agglutination tests and ELISA tests.

The presence of cold agglutinins, which is suggestive at a level>64, is sometimes observed in *M. pneumoniae* infections, but it is neither consistent nor characteristic. This technique, which has been used in the past, is therefore no longer recommended for detecting *M. pneumoniae* infection.

The complement fixation reaction (CFR), which uses an antigen preparation produced from the whole microorganism, has been used for a long time. The test measures the level of IgM and IgG simultaneously, without distinguishing between them. A level>64 is suggestive of an infection. The technique is cumbersome, of low sensitivity and can give rise to cross-reactions or results that cannot be interpreted ("anti-complementary" serums).

The detection of specific antibodies can be carried out by indirect immunofluorescence. The serum to be tested, brought into contact with *M. pneumoniae* antigens, is revealed by human anti-IgM or anti-IgG antibodies conjugated to a fluorochrome. This technique exists in the form of a commercial kit but requires a fluorescence microscope. Reading of the slides is long and laborious and interpretation of the results remains tricky.

Passive agglutination tests for the detection of IgM and/or IgG are commercially available. They reveal the recognition, by antibodies contained in the patient's serum, of antigens (extracted from *M. pneumoniae*) fixed to particles of latex, of gelatin or of erythrocytes in the case of the indirect hemagglutination test (IHA). The technique requires at least two serums in order to reveal an increase in the antibody titer and does not have advantages over the ELISA technique (Waites K. B., C. M. Bébéar, J. A. Robertson, D. F. Talkington and G. E. Kenny. Laboratory diagnosis of mycoplasmal infections. Cumitech of American Society for Microbiology, coordinating editor: F. S. Nolte, 2002, ASM press: 1-30).

The ELISA techniques allow IgGs or IgMs to be detected independently. Preparations of bacterial extracts, of purified proteins such as adhesin P1, of glycolipids, of synthetic peptides have been used, fixed to the solid support. The patients' serum is incubated with the solid antigen phase and human anti-IgG or anti-IgM antibodies conjugated to an enzyme reacting with the antibodies bound to the antigen. The complex is revealed by the hydrolysis of a substrate of the enzyme, resulting in a stained product. The choice of ELISA (IgM and/or IgG) depends on the age of the patient and on the number of serums which can be tested. The presence of IgM is very suggestive in children and adolescents but is more rarely observed in adults. It is preferable to detect specific antibodies on two serums taken at a 10-15 day interval, in order to reveal a seroconversion (increase×4 of the antibody titer).

In summary, current practices do not always meet medical expectations in establishing a definite diagnosis of *M. pneumoniae* infections in children or adults. Although serological tests appear to be most suitable, the diagnosis of an active infection in many cases remains difficult to distinguish from that of a past infection (Waites K. B., C. M. Bébéar, J. A. Robertson, D. F. Talkington and G. E. Kenny. Laboratory diagnosis of mycoplasmal infections. Cumitech of American Society for Microbiology, coordinating editor: F. S. Nolte, 2001, ASM press; 1-30, Talkington D F, Shott S, Fallon M T, Schwartz S B and Thacker W L. Analysis of eight commercial enzyme immunoassay tests for detection of antibodies to *Mycoplasma pneumoniae* in human serum, Clin. Diagn. Lab. Immunol., 2004).

The objects of the present invention are especially to resolve the deficiencies of current serological tests and to permit a sensitive and specific diagnosis of *Mycoplasma pneumoniae* infections. It is within this context that the inventors of the present invention have identified, from the genome of *M. pneumoniae*, a polypeptide called 7F4, corresponding to the beta-subunit of ATPase, having the polypeptide sequence SEQ ID NO: 2, the possible uses of which, including that indicated hereinbelow, are described below. The 7F4 protein is a membrane protein exposed in the cytoplasm of the bacterium and involved in the metabolic activity of *M. pneumoniae*. It is also found in other microorganisms, especially other species of mycoplasms such as *M. hypopneumoniae*.

DEFINITIONS

The following definitions are given in order to facilitate the comprehension of some terms used in this description.

"Polynucleotide" is understood as being a polyribonucleotide or a polydeoxyribonucleotide which can be a modified or unmodified DNA or RNA.

The term polynucleotide includes, without limitation, a single-stranded or double-stranded DNA, a DNA composed of a mixture of one or more single-stranded region(s) and of one or more double-stranded region(s), a DNA which is a mixture of single-stranded, double-stranded and/or triple-stranded regions, a single-stranded or double-stranded RNA, an RNA composed of a mixture of one or more single-stranded region(s) and of one or more double-stranded region(s), and hybrid molecules comprising a DNA and an RNA which can comprise single-stranded, double-stranded and/or triple-stranded regions or a mixture of single-stranded and double-stranded regions. The term polynucleotide can also include an RNA and/or DNA comprising one or more triple-stranded regions. The strands in such regions can originate from the same molecule or from different molecules. Consequently, DNAs or RNAs having backbones modified for stability, or for other reasons, are included in the term polynucleotides. Polynucleotide is also understood as meaning DNAs and RNAs containing one or more modified bases. "Modified base" is understood as meaning, for example, unusual bases such as inosine. The term polynucleotide also refers to polynucleotides of chemically, enzymatically or metabolically modified form. Polynucleotides also include short polynucleotides such as oligonucleotides.

A "polypeptide" is understood as being a peptide, an oligopeptide, an oligomer or a protein comprising at least two amino acids joined together by a normal or modified peptide bond.

The term polypeptide includes short chains, called peptides, oligopeptides and oligomers, and long chains, called proteins.

A polypeptide can be composed of amino acids other than the amino acids coded for by human genes. A polypeptide can also be composed of amino acids modified by natural processes, such as the process of post-translational maturation, or by chemical processes, which are known to the person skilled in the art. The same type of modification can be present at several sites of the polypeptide and anywhere in the polypeptide: in the peptide backbone, in the amino acid chain or at the carboxy- or amino-terminal ends.

A polypeptide can be branched following a ubiquitination or can be cyclic with or without branching. This type of modification can be the result of natural or synthetic post-translation processes, which are known to the person skilled in the art.

Modifications of a polypeptide are understood as being, for example, acetylation, acylation, ADP-ribosylation, amidation, the covalent binding of flavin, the covalent binding of a heme, the covalent binding of a nucleotide or nucleotide derivative, the covalent binding of a lipid or lipid derivative, the covalent binding of a phosphatidyl-inositol, covalent or non-covalent crosslinking, cyclization, disulfide bridge formation, demethylation, cysteine formation, pyroglutamate formation, formylation, gamma-carboxylation, glycosylation, GPI anchor formation, hydroxylation, iodization, methylation, myristoylation, oxidation, the proteolytic process, phosphorylation, prenylation, racemization, seneloylation, sulfatation, addition of amino acids, such as arginylation or ubiquitination (PROTEINS STRUCTURE AND MOLECULAR PROPERTIES, 2nd Ed., T. E. Creighton, W.H. Freeman and Company, New York (1993) and Wold, F., Posttranslational Protein Modifications: Perspectives and Prospects, pgs 1-12 in POSTTRANSLATIONAL COVALENT MODIFICATION OF PROTEINS, B. C. Johnson, Ed., Academic Press, New York (1983); Seifter et al., Meth. Enzymol. 182: 626-646 (1990) and Rattan et al., Protein Synthesis: Posttranslational Modifications and Aging, Ann. N.Y. Acad. Sci. 663: 48-62 (1992)).

"Isolated" is understood as meaning modified by the human hand from the natural state, that is to say that the polynucleotide or polypeptide present in nature has been modified or isolated from its natural environment, or both. For example, a polynucleotide or a polypeptide naturally present in a living organism is not "isolated", but the same polynucleotide or polypeptide separated from the materials coexisting in its natural state is "isolated".

The "percentage identity" between two polynucleotide or polypeptide sequences is understood as being the percentage of nucleotides or amino acids that are identical between the two sequences to be compared, which is obtained after the best alignment, that percentage being purely statistical and the differences between the two sequences being randomly distributed over their entire length. Comparisons between two polynucleotide or polypeptide sequences are conventionally made by comparing the sequences after they have been optimally aligned, said comparison being carried out per segment or per "comparison window" in order to identify and compare the local regions having sequence similarity. The comparison can be made by means of a program, for example the EMBOSS-Needle program (Needleman-Wunsch overall alignment) with the aid of the BLOSUM62 matrix/Open Gap 10.0 and Extension Penalty of 0.5 (Needleman, S. B. and Wunsch, C. D. (1970), J. Mol. Biol. 48, 443-453 and Kruskal, J. B. (1983), An overview of sequence comparison, in D. Sankoff and J. B. Kruskal, (ed), Time warps, strind edits and macromolecules: the theory and practice of sequence comparison, pp. 1-44 Addison Wesley).

The percentage identity is calculated by determining the number of identical positions for which the nucleotide or amino acid is identical between the two sequences, dividing that number of identical positions by the total number of positions in the comparison window, and multiplying the result obtained by 100.

A polypeptide having, for example, an identity of at least 95% with the polypeptide SEQ ID NO: 2 is a polypeptide comprising, at most, 5 modified amino acids out of 100 amino acids, relative to said sequence. In other words, up to 5% of the amino acids in the sequence SEQ ID NO: 2 can be deleted or substituted by a different amino acid or the sequence can comprise up to 5% amino acids in addition, relative to the total number of amino acids in the sequence SEQ ID NO: 2. These alterations to the sequence can be situated at the amino- and/or carboxy-terminal positions of the amino acid sequence or at any site between those terminal positions, in one or more locations (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987).

By analogy, a polynucleotide having, for example, an identity of at least 95% with the polynucleotide SEQ ID NO: 1 is therefore a polynucleotide comprising, at most, 5 modified nucleotides out of 100, relative to the sequence of said polynucleotide. In other words, up to 5% of the nucleotides of the polynucleotide SEQ ID NO: 1 can be deleted or substituted by a different nucleotide, or a polynucleotide can comprise up to 5% nucleotides in addition, relative to the total number of nucleotides of the polynucleotide SEQ ID NO: 1. These modifications can be positioned at the 3' and/or 5' ends or at any site between those ends, in one location or in a plurality of locations.

A "polypeptide fragment" is understood as being a polypeptide comprising at least "n" consecutive amino acids obtained from the polypeptide SEQ ID NO: 2 where, depending on the sequences, n will be equal to 7 amino acids or more (for example 8, 10, 12, 14, 16, 18, 20, 30, 40, 50 or more amino acids). Preferably, said fragments comprise an epitope of the sequence SEQ ID NO: 2. These epitopes of type B or T can be determined by a software program (for example PEOPLE [Alix, 1999], PREDITOP [Pellequer and Westhof, 1993] or TEST [Zao et al., 2001] or by means of experiment by conventional techniques [for example epitope mapping or mild proteolysis].

A "polynucleotide fragment" is understood as being a polynucleotide comprising at least "n" consecutive nucleotides obtained from the polynucleotide SEQ ID NO: 1, where, depending on the sequences, n will be equal to 21 nucleotides or more (for example 22, 23, 24, 25, 30, 36, 42, 48, 54, 60, 90, 120, 150 or more nucleotides).

A "host cell" is understood as being a cell which has been transformed or transfected, or which is capable of being transformed or transfected, by an exogenous polynucleotide sequence.

"Specific primers" are understood as being short nucleotide sequences capable of hybridizing specifically, owing to the complementarity of the bases, to the DNA strand or to its complementary strand.

"Culture medium" is understood as being the medium in which the polypeptide of the invention is purified. The medium can be constituted by the extracellular medium and/or the cellular lysate. Techniques known to the person skilled in the art also enable the active conformation to be returned to the polypeptide if the conformation of said peptide was modified during isolation or purification.

"Function" is understood as meaning the biological activity of a polypeptide or polynucleotide. The function of a polypeptide according to the invention is that of an *M. pneumoniae* antigen, and the function of a polynucleotide according to the invention is to code for the polypeptide.

An "antigen" is understood as being any compound which, on its own or in association with an adjuvant or carrier, is capable of inducing a specific immune response. This definition also includes any compound having structural analogy with said antigen capable of inducing an immunological response directed against said antigen.

"Structural analogy" is understood as meaning analogy both of the primary structure (sequence) and of the secondary structure (structural elements), of the tertiary structure (three-dimensional structure) or of the quaternary structure (association of several polypeptides in a single complex) (BIOCHEMISTRY, 4th Ed., L. Stryer, New York, 1995).

A "variant" of a so-called initial polynucleotide or of a so-called initial polypeptide, respectively, is understood as being a polynucleotide or polypeptide which differs therefrom by at least one nucleotide or amino acid, but which retains the same intrinsic properties, that is to say the same function.

A difference in the polynucleotide sequence of the variant may or may not alter the amino acid sequence of the polypeptide for which it codes, relative to an initial polypeptide. Nevertheless, by definition, these variants must confer the same function as the initial polynucleotide sequence, for example must code for a polypeptide having an antigenic function.

The variant polynucleotide or polypeptide generally differs from the initial polynucleotide or the initial polypeptide by one (or more) substitution(s), addition(s), deletion(s), fusion(s) or truncation(s), or a plurality of those modifications, taken in combination. An unnatural variant of an initial polynucleotide or of an initial polypeptide can be obtained, for example, by site-directed mutagenesis or by direct synthesis.

A "polynucleotide sequence complementary to the polynucleotide sequence" is defined as a polynucleotide which can be hybridized with that polynucleotide sequence under stringent conditions.

"Stringent conditions" are generally, but not necessarily, understood as being the chemical conditions that permit a hybridization when the polynucleotide sequences have an identity of at least 80%. These conditions can be obtained according to methods known to the person skilled in the art.

"Antibodies" are understood as being monoclonal, polyclonal, chimeric, single-chain, humanized antibodies as well as Fab fragments, including the products of an Fab or of an immunoglobulin expression library.

An immunospecific antibody can be obtained by administering a given polypeptide to an animal and then recovering the antibodies produced by said animal by extraction from its body fluids. It is also possible to administer to the animal a variant of said polypeptide or host cells expressing the polypeptide.

The term "immunospecific" applied to the term antibody, in respect of a given polypeptide, means that the antibody has a better affinity for that polypeptide than for other polypeptides known in the prior art.

"Affinity" is understood as meaning both a structural complementarity and a complementarity of the low-energy bonds between two molecules in the sense of a commonly established definition (see, for example, Klotz I M, Ligand-protein binding affinities. In *Protein Function, a Practical Approach* (T. E. Creighton, Ed.). 1989; 25-35. IRL Press, Oxford, or Ajay, Murcko Mass. Computational methods to predict binding free energy in ligand-receptor complexes. J Med Chem. 1995; 38: 4953-67). The affinity can be measured by the conventional techniques of biochemistry (ELISA, competition, fluorescence, etc.) known to the person skilled in the art.

A "positive" serum is understood as being a serum containing antibodies, produced following an *M. pneumoniae* infection, identified by their binding with the polypeptide (antigen) of the invention.

"Sensitivity" is understood as meaning the proportion of infected patients, diagnosed according to the prior art and given as positive by the diagnosis according to the invention.

"Specificity" is understood as meaning the proportion of blood donors, tested as controls, subjected to the diagnosis according to the invention and given as negative by the diagnosis according to the invention.

A "diagnostic kit" is understood as being a set containing at least one of the products according to the invention (polypeptide, polynucleotide) and a suitable diluent, combined in an appropriate container made of a suitable material. This container can hold the various additional means necessary for the serological test (for example labelled reagents, buffers, solutions containing suitable ions, etc.) as well as the required instructions for carrying out the test.

As indicated hereinbefore, the invention relates to the use, in the field of the in vitro diagnosis of *M. pneumoniae* infections and/or in the production of vaccines against *M. pneumoniae*, of polypeptides according to the invention, of polynucleotides coding for said polypeptides, of expression vectors comprising said polynucleotides, of host cells comprising said expression vectors.

Use of Polypeptides

The identification of the polypeptide according to the invention is the result of a screening and of in-depth studies which could not be envisaged from the sequences obtained from the *M. pneumoniae* genomic programs.

The present invention accordingly relates to the use of an isolated polypeptide comprising amino acid sequence SEQ ID NO: 2 (called 7F4 protein), coded for by the polynucleotide sequence SEQ ID NO: 1, for the in vitro detection, in biological samples, of the presence of antibodies produced following a *Mycoplasma pneumoniae* infection. The present invention relates also to the use of an isolated polypeptide comprising:
a) a fragment of the amino acid sequence SEQ ID NO: 2 having the same function as the sequence SEQ ID NO: 2, or
b) an amino acid sequence having at least 60% identity, preferably at least 80% identity, and better still at least 90% identity, with the amino acid sequence SEQ ID NO: 2, or with the fragment of sequence defined under a), and having the same function as sequence SEQ ID NO: 2.

The present invention relates also to a process for the preparation of a polypeptide as defined above, in which a host cell defined hereinbefore is cultured and said polypeptide is isolated from the culture medium.

The polypeptide can be purified from the host cells, according to methods known to the person skilled in the art, such as precipitation with the aid of chaotropic agents such as salts, in particular ammonium sulfate, ethanol, acetone or trichloroacetic acid, or by means such as acid extraction, ion-exchange chromatography, chromatography on phosphocellulose, hydrophobic interaction chromatography, affinity chromatography, chromatography on hydroxylapatite or exclusion chromatography.

Use of Polynucleotides

The present invention relates especially to the use in the in vitro detection, in biological samples, of the presence of antibodies produced following a *Mycoplasma pneumoniae* infection of an isolated polynucleotide comprising the polynucleotide sequence SEQ ID NO: 1 coding for the polypeptide comprising the amino acid sequence SEQ ID NO: 2. The invention relates also to the use of an isolated polynucleotide comprising:

a) a fragment of the sequence SEQ ID NO: 1 having the same function as the sequence SEQ ID NO: 1, or
b) a polynucleotide sequence having at least 60% identity, preferably at least 80% identity, and better still at least 90% identity, with the polynucleotide sequence SEQ ID NO: 1, or with the fragment of sequence as defined under a), and having the same function as sequence SEQ ID NO: 1, or
c) a polynucleotide sequence which is complementary to the polynucleotide sequence SEQ ID NO: 1 or to the fragment of sequence defined under a) or to the sequence defined under b).

Accordingly, polynucleotides according to the invention can comprise variants or fragments of the polynucleotide sequence SEQ ID NO: 1.

The polynucleotides of the invention can be obtained by standard methods of DNA or RNA synthesis.

The polynucleotides according to the invention can likewise comprise polynucleotide sequences such as the 5' and/or 3' non-coding sequences, such as, for example, transcribed sequences, untranslated sequences, splice signal sequences, polyadenylated sequences, ribosome binding sequences or mRNA-stabilizing sequences.

Use of Expression Vectors and of Host Cells

The present invention relates also to the use of the polypeptide according to the invention prepared by culturing a host cell comprising a recombinant vector having, inserted, a polynucleotide coding for said polypeptide according to the invention.

Numerous expression systems can be used, such as, for example, chromosomes, episomes, derived viruses. More particularly, the recombinant vectors used can be derived from bacterial plasmids, transposons, yeast episome, insertion elements, yeast chromosomal elements, viruses such as baculoviruses, papilloma viruses such as SV40, vaccinia viruses, adenoviruses, fox pox viruses, pseudorabies viruses, retroviruses.

These recombinant vectors can also be cosmid or phagemid derivatives. The polynucleotide sequence can be inserted into the recombinant expression vector by methods known to the person skilled in the art.

The recombinant vector can comprise polynucleotide sequences for controlling the regulation of the expression of the polynucleotide as well as polynucleotide sequences permitting the expression and transcription of a polynucleotide of the invention and the translation of a polypeptide of the invention, those sequences being chosen as a function of the host cells used.

The introduction of the recombinant vector into a host cell can be carried out according to methods known to the person skilled in the art, such as transfection by calcium phosphate, transfection by cationic lipids, electro-poration, transduction or infection.

The host cells can be, for example, bacterial cells, such as cells of streptococci, staphylococci, *Escherichia coli* or *Bacillus subtilis*, fungal cells, such as yeast cells and *Aspergillus* cells, *Streptomyces* cells, insect cells, such as *Drosophilia* S2 cells and *Spodoptera* Sf9 cells, animal cells, such as CHO, COS, HeLa, C127, BHK, HEK 293 cells, or plant cells.

The polypeptide can be purified from the host cells according to methods known to the person skilled in the art, such as precipitation with the aid of chaotropic agents, such as salts, in particular ammonium sulfate, ethanol, acetone or trichloroacetic acid, or by means such as acid extraction, ion-exchange chromatography, chromatography on phosphocellulose, hydrophobic interaction chromatography, affinity chromatography, chromatography on hydroxylapatite, or exclusion chromatography.

Serology

The biological samples tested can be blood, urine, saliva, serological puncture fluid (for example cerebrospinal fluid, pleural fluid or articular fluid) or a constituent thereof (for example serum).

Vaccines

The present invention relates also to a pharmaceutical composition which can be used as a vaccine and which comprises as active ingredient at least one of the polypeptide, polynucleotide, recombinant vector or host cell according to the invention and a pharmaceutically acceptable excipient (for example a sterile or non-sterile aqueous solution which can contain an antioxidant or a buffer or a solute which renders the composition isotonic for body fluids).

Kits

The invention relates also to in vitro diagnostic kits comprising, on the one hand:
  at least one of the polypeptides according to the invention, or
  at least one of the polynucleotides coding for said polypeptides,
and, on the other hand, at least one diluent (for example a buffer, saline solution, etc.) and a notice of instructions for use.

EXPERIMENTAL PART

A) Protocol for Obtaining Antigens
A. 1) Cloning of the Sequence Coding for the Polypeptide SEQ ID NO: 2

The gene coding for the sequence of the polypeptide 7F4 according to the invention, which is an antigen, is obtained by PCR amplification from the genomic DNA of the bacterium *M. pneumoniae* (strain M129-B7, ATCC 29342) using as primer pair:
the sense oligonucleotide containing the sequence: 5'-AAAAAGGAAAACATTACATACG-3' (SEQ ID NO: 3); and the antisense oligonucleotide containing the sequence: 5'-TTTCTCCTCAACAGTAG-3' (SEQ ID NO: 4).

The corresponding fragment, so amplified, is cloned into a vector according to conventional techniques known to the person skilled in the art. This vector permits the production of the cloned protein under the control of a promoter inducible by isopropyl thiogalactoside (abbreviation IPTG). The cloned protein corresponds to the amino acid sequence SEQ ID NO: 2.

A. 2) Expression of the Protein

An *Escherichia coli* strain is transformed with the expression vector described hereinbefore. The selected bacteria are cultured overnight at 30° C., with stirring, in 50 ml of Luria Bertani medium (LB, J. Miller, "A short course in Bacteria Genetics", Cold Spring Harbor Laboratory Press, 1992) containing ampicillin and chlormaphenicol both at a final concentration of 100 µg/ml. On the following day, the culture is diluted 1/50 in a final volume of 1 litre of LB medium supplemented with ampicillin and chloramphenicol, both at a final concentration of 100 µg/ml, and is incubated at 30° C., with stirring. When the turbidity of the culture reaches an absorbance value at 600 nm (abbreviation A600) of approximately 0.7, the production of the protein is induced by isopropyl thiogalactoside (IPTG) at a final concentration of 0.5 mM. The bacteria are harvested by centrifugation (6 minutes at 5240 rpm at 4° C.) when the turbidity of the culture reaches an A600 of approximately 1.5.

A. 3) Purification

After centrifugation, the cells are resuspended in a 20 mM Tris-HCl buffer at pH 8 containing 0.5 mM sucrose, and are then treated with lysozyme (0.1 g/50 ml) in the presence of 250 mM ethylenediaminetetraacetic acid (EDTA). The suspension is incubated for 30 minutes at 4° C. and then centrifuged for 10 minutes at 4° C. at 15,500×g. The pellet is frozen at −20° C. for at least one night.

After thawing, the bacteria are taken up in a 25 mM Mes [2-(N-morpholino)ethanesulfonic acid] buffer at pH 6.0 and then sonicated 4 times for 20 seconds in ice. After centrifugation at 15,500 g at 4° C. for 30 minutes, the pellets are taken up in 10 ml of 25 mM Mes buffer at pH 6.0, 8 M urea, 20 mM β-mercaptoethanol. The suspension is then centrifuged for 20 minutes at 14,000 rpm at ambient temperature (AT). The supernatant is again centrifuged for 30 minutes at AT at 14,000 rpm and is then filtered over a membrane of porosity 0.22 µm. The filtrate is then deposited on a cation-exchange column (for example SP-Sepharose 12 ml, Amersham Biosciences). After washing the column, the protein is eluted with a linear gradient of 0 to 1 M of NaCl in 25 mM Mes buffer at pH 6.0, 8 M urea, 20 mM β-mercaptoethanol in 20 column volumes. The fractions containing the protein are collected, dialyzed overnight against 25 mM Mes buffer at pH 6.0, 8 M urea, 20 mM β-mercaptoethanol and are then redeposited on the same column. The protein is then eluted with a fresh NaCl gradient optimized for the 7F4 protein. The chosen protein-containing fractions are collected and then dialyzed overnight against 50 mM Na$_2$HPO$_4$/NaH$_2$PO$_4$ buffer at pH 8.0 containing 100 mM NaCl and are then deposited on a gel filtration column (for example Superdex HR75-10/30, Amersham). The eluted protein-containing fractions are collected and stored at ambient temperature until used in the tests.

The protein concentrations are determined from the molar absorption coefficients calculated by the Pace method (Pace C N, Vajdos F., Fee L., Grismley G. and Gray T., (1995), Protein Science 4, 2411-2423). The purity of the proteins is checked by SDS-PAGE electrophoretic analysis.

B) In Vitro Diagnostic Test

Serums obtained from child and adult patients who have had a documented *M. pneumoniae* infection (laboratory collection; i.e. positive IgM and/or IgG and/or RFC titer and/or positive PCR and/or positive culture).

The control serums correspond to serums from blood donors (laboratory collection).

Fixing, to the purified recombinant protein 7F4 (obtained as described hereinbefore), of the antibodies present in the serums was evaluated either by Western Blot tests or by the ELISA technique.

Example B. 1

Western Blot Test Protocol for the Polypeptides According to the Invention

After transfer of the purified 7F4 protein to a nitro-cellulose membrane, the membrane is saturated for 45 minutes with the aid of a phosphate buffered saline (PBS) solution containing 3% semi-skimmed milk. After washing three times with PBS containing 0.05% polyoxyethylene sorbitan (Tween), the membrane is exposed to the test serum at the appropriate dilution (1/500) in PBS buffer containing 3% semi-skimmed milk for 45 minutes. After washing for a further three times, goat anti-human immunoglobulin G and A and M antibodies (for example 170-1042, Biorad), labelled with alkaline phosphatase, are added for a period of 45 minutes after being diluted according to the supplier's protocol in PBS buffer containing 3% semi-skimmed milk. Washing was carried out a further three times, and then 5-bromo-4-chloro-3-indolyl phosphate and nitroblue tetrazolium are added according to the supplier's instructions until the result is obtained. A "positive" result corresponds to the fixing of the anti-human immunoglobulin antibody to a complex composed of the polypeptide according to the invention fixed to the membrane and of the human serum antibody that specifically recognizes it, which manifests itself by local staining of said complex.

Example B. 2

ELISA Test Protocol

The ELISA plates are left overnight at ambient temperature in the presence of 0.5 µg of purified antigen (recombinant 7F4 protein) in phosphate buffered saline (PBS)—6 M urea. After washing four times with PBS containing 0.05% polyoxyethylene sorbitan (Tween), the plates are saturated for one hour and a half at 37° C. with PBS-Tween containing 4% bovine serum albumin (BSA) (250 µl per well). Washing is carried out a further four times, and then 100 µl of each serum to be tested are added, diluted 1/100 in 4% PBS-BSA buffer, to each well. The plate is then incubated at 37° C. for 30 minutes. After washing a further four times, anti-human immunoglobulin G and/or A and/or M antibodies labelled with peroxydase (for example 31415, Pierce) are added (simultaneously and/or independently) for 30 minutes at 37° C. after being diluted, according to the supplier's protocol, in 4% PBS-BSA buffer. Washing is carried out a further four times, and then 100 µl of tetrabenzimidine (TMB) substrate (for example HD979505, Pierce) are added per well. After incubation for about 15 minutes, 100 µl of sulfuric acid are added to each well. The absorbance at 450 nm of each well is then measured after 5 minutes.

Serums identified by their binding to the polypeptides (antigens) of the invention are considered to be "positive" in ELISA.

C) Results and Interpretations

A typical result obtained is presented in the table below. The serums from patients (children and/or adults) considered to be positive are those containing antibodies directed against *M. pneumoniae*, identified by ELISA by their binding to the polypeptides (antigens) of the invention.

Table of results (ELISA) obtained in adult and/or child patients using anti-IgMs as secondary antibodies

| | |
|---|---|
| Number of "positive" serums among the 62 serums of patients (children and adults) infected by *M. pneumoniae* diagnosed according to the prior art and subjected to the diagnosis according to the invention | 32 (i.e. 51.6%) |
| Number of "positive" serums among the 34 serums of child patients infected with *M. pneumoniae* diagnosed according to the prior art and subjected to the diagnosis according to the invention | 24 (i.e. 70.6%) |
| Number of "positive" serums among the 28 serums of adult patients infected with *M. pneumoniae* diagnosed according to the prior art and subjected to the diagnosis according to the invention | 8 (i.e. 28.5%) |
| Number of "negative" serums among the 96 serums of control blood donors | 92 (i.e. 95.8%) |

Significant results can also be obtained using anti-IgA antibodies as secondary antibodies. Likewise, similar results can be obtained by Western Blot.

According to the table of results, it is noted that, by the ELISA test, it is possible to identify in vitro at least 51.6% of the *M. pneumoniae* infections whatever the age of the patient, at least 70.6% of the *M. pneumoniae* infections in child patients and at least 28.5% of the *M. pneumoniae* infections in adult patients by means of the antigen according to the invention.

It is therefore shown, on the one hand, that in humans there is a significant antibody response (the probability associated with a $\chi2$ test is less than 0.05) in respect of the 7F4 protein during *M. pneumoniae* infections and, on the other hand, that the 7F4 protein is pertinent for the serological diagnosis of this type of infection, in particular in children.

A high level of anti-7F4 antibodies is noted in most of the children tested. This antigen can therefore confer on infected individuals lasting immune protection against reinfection. The 7F4 antigen could therefore be used for vaccination against *M. pneumoniae* infections.

The invention claimed is:

1. A method for determining if a human individual is infected by *Mycoplasma pneumonia*, comprising:
    contacting a biological sample of the individual with a purified protein comprising SEQ ID NO: 2;
    testing said contacted samples for the presence of antibodies bound to said protein comprising SEQ ID NO: 2, indicating that the individual is infected by *Mycoplasma pneumoniae*; and
    deducing therefrom if the individual is infected by *Mycoplasma pneumoniae*.

2. The method of claim 1, wherein the biological sample is selected from the group consisting of: blood, serum, urine, saliva, cerebrospinal fluid, pleural fluid, and articular fluid.

3. A method for determining the presence of antibodies directed against *Mycoplasma pneumoniae* in a biological sample from a human individual comprising:
    contacting the biological sample with a purified protein comprising SEQ ID NO: 2; and
    testing said contacted samples for antibodies bound to said protein comprising SEQ ID NO: 2,
    wherein a detection of antibodies bound to said protein comprising SEQ ID NO: 2 indicates that the individual is infected by *Mycoplasma pneumoniae*.

4. The method of claim 3, wherein the biological sample is selected from the group consisting of: blood, serum, urine, saliva, cerebrospinal fluid, pleural fluid, and articular fluid.

* * * * *

SEQUENCE LISTING

<160> NUMBER OF SEQ ID NOS: 4

<210> SEQ ID NO 1
<211> LENGTH: 1422
<212> TYPE: DNA
<213> ORGANISM: Mycoplasma pneumoniae
<220> FEATURE:
<221> NAME/KEY: CDS
<222> LOCATION: (1)..(1422)

<400> SEQUENCE: 1

```
aaa aag gaa aac att aca tac ggt aag gtc cac caa gtg att ggc ccg      48
Lys Lys Glu Asn Ile Thr Tyr Gly Lys Val His Gln Val Ile Gly Pro
1               5                   10                  15 gta gtt gat gtc atc ttt acg gaa agt agt cag tta ccc cgc att tac      96
Val Val Asp Val Ile Phe Thr Glu Ser Ser Gln Leu Pro Arg Ile Tyr
                20                  25                  30 gat tgt ttg agt gtt aag tta gct ggg gaa gaa ctg ttt ttg gaa gcc     144
Asp Cys Leu Ser Val Lys Leu Ala Gly Glu Glu Leu Phe Leu Glu Ala
            35                  40                  45 gcg cag cta ata ggc gat gac att gtg cgc tgc att gct ttg ggt cca     192
Ala Gln Leu Ile Gly Asp Asp Ile Val Arg Cys Ile Ala Leu Gly Pro
        50                  55                  60 act gaa ggg tta gca cgc aac gaa aag gtg act aac tat aac cac ccg     240
Thr Glu Gly Leu Ala Arg Asn Glu Lys Val Thr Asn Tyr Asn His Pro
65                  70                  75                  80 att gaa gtc cca gtt ggc aaa aac gtc ttg ggc cgg atg ttt aat gtt     288
Ile Glu Val Pro Val Gly Lys Asn Val Leu Gly Arg Met Phe Asn Val
                85                  90                  95 ttg ggt aaa ccc att gac ggg aag gag gag tta ccc aaa aaa cca caa     336
Leu Gly Lys Pro Ile Asp Gly Lys Glu Glu Leu Pro Lys Lys Pro Gln
                100                 105                 110 ctc ccg att cac cgc aaa cca cct tcg ttt gat gac cag tcc aat acg     384
Leu Pro Ile His Arg Lys Pro Pro Ser Phe Asp Asp Gln Ser Asn Thr
            115                 120                 125 cta gaa atc ttt gaa aca ggg att aag gtg att gac ttg ctc act ccc     432
Leu Glu Ile Phe Glu Thr Gly Ile Lys Val Ile Asp Leu Leu Thr Pro
        130                 135                 140
```

```
tat gcc cgt ggt ggt aag att ggt tta ttt ggt ggt gct ggt gtt ggt      480
Tyr Ala Arg Gly Gly Lys Ile Gly Leu Phe Gly Gly Ala Gly Val Gly
145                 150                 155                 160 aaa acg gtt tta gtg caa gag tta atc cac aac att gct aag gaa cac      528
Lys Thr Val Leu Val Gln Glu Leu Ile His Asn Ile Ala Lys Glu His
                165                 170                 175 tct ggt tta agt gtg ttt gct ggt gtg ggg gaa cgc acc cgg gaa ggt      576
Ser Gly Leu Ser Val Phe Ala Gly Val Gly Glu Arg Thr Arg Glu Gly
            180                 185                 190 aat gat ctc tac tat gaa atg atc cag ggt ggg gta att gac aaa act      624
Asn Asp Leu Tyr Tyr Glu Met Ile Gln Gly Gly Val Ile Asp Lys Thr
        195                 200                 205 gct tta gtg ttt ggt cag atg aac gaa ccc cca gga gca cgg atg cgg      672
Ala Leu Val Phe Gly Gln Met Asn Glu Pro Pro Gly Ala Arg Met Arg
    210                 215                 220 gtc gct tta acg gcg ctt act atg gcc gaa tac ttc cgt gac cat gac      720
Val Ala Leu Thr Ala Leu Thr Met Ala Glu Tyr Phe Arg Asp His Asp
225                 230                 235                 240 aac cag gat gtc ttg ctc ttc att gac aac atc ttc cgt ttt acc caa      768
Asn Gln Asp Val Leu Leu Phe Ile Asp Asn Ile Phe Arg Phe Thr Gln
                245                 250                 255 gct ggt agt gag gta tca gca ctg tta ggt cgg atg cca tca gcc gtg      816
Ala Gly Ser Glu Val Ser Ala Leu Leu Gly Arg Met Pro Ser Ala Val
            260                 265                 270 ggt tac caa cca acg ttg gcg act gaa atg ggg caa tta caa gag cgg      864
Gly Tyr Gln Pro Thr Leu Ala Thr Glu Met Gly Gln Leu Gln Glu Arg
        275                 280                 285 att gct tcc act aaa acc ggt tcg att acc tcg gtg caa gcg atc tat      912
Ile Ala Ser Thr Lys Thr Gly Ser Ile Thr Ser Val Gln Ala Ile Tyr
    290                 295                 300 gtg cca gct gat gac ttg act gac ccc gct ccg gct acc acc ttt acc      960
Val Pro Ala Asp Asp Leu Thr Asp Pro Ala Pro Ala Thr Thr Phe Thr
305                 310                 315                 320 cac ctg gat gct aaa acg gtg tta gac cgg aac ata gca gcg ttg gga     1008
His Leu Asp Ala Lys Thr Val Leu Asp Arg Asn Ile Ala Ala Leu Gly
                325                 330                 335 att ttt cca gcg atc aat ccc tta gag tct acc agt cgc tta ttg gat     1056
Ile Phe Pro Ala Ile Asn Pro Leu Glu Ser Thr Ser Arg Leu Leu Asp
            340                 345                 350 cct aat att gtc ggg att aac cac tat aag gta gcg tta ggg atg caa     1104
Pro Asn Ile Val Gly Ile Asn His Tyr Lys Val Ala Leu Gly Met Gln
        355                 360                 365 aac atc tta cag cgc ttt gcg gaa cta caa gac att att gcc atc ttg     1152
Asn Ile Leu Gln Arg Phe Ala Glu Leu Gln Asp Ile Ile Ala Ile Leu
    370                 375                 380 gga att gat gag tta gcg gat gag gac aag atc att gtg gaa cgg gca     1200
Gly Ile Asp Glu Leu Ala Asp Glu Asp Lys Ile Ile Val Glu Arg Ala
385                 390                 395                 400 cgc cgg atc cgc aac ttc ctc tcc caa ccg ttc ttt gta gcg gaa aag     1248
Arg Arg Ile Arg Asn Phe Leu Ser Gln Pro Phe Phe Val Ala Glu Lys
                405                 410                 415 ttc tcg ggg att gct ggg aag tat gtc cct tta agt gac acg atc caa     1296
Phe Ser Gly Ile Ala Gly Lys Tyr Val Pro Leu Ser Asp Thr Ile Gln
            420                 425                 430 tcg ttt aag gaa atc ttg gac ggt aag cat gat gat ctc ccc gaa cag     1344
Ser Phe Lys Glu Ile Leu Asp Gly Lys His Asp Asp Leu Pro Glu Gln
        435                 440                 445 gcc ttc ttc ttt gtt ggt acc att cag gaa gca gtg gag aaa gcg aag     1392
Ala Phe Phe Phe Val Gly Thr Ile Gln Glu Ala Val Glu Lys Ala Lys
450                 455                 460
```

```
cgg ctt aaa aaa gct act gtt gag gag aaa                          1422
Arg Leu Lys Lys Ala Thr Val Glu Glu Lys
465             470
```

<210> SEQ ID NO 2
<211> LENGTH: 474
<212> TYPE: PRT
<213> ORGANISM: Mycoplasma pneumoniae

<400> SEQUENCE: 2

```
Lys Lys Glu Asn Ile Thr Tyr Gly Lys Val His Gln Val Ile Gly Pro
1               5                   10                  15

Val Val Asp Val Ile Phe Thr Glu Ser Ser Gln Leu Pro Arg Ile Tyr
            20                  25                  30

Asp Cys Leu Ser Val Lys Leu Ala Gly Glu Glu Leu Phe Leu Glu Ala
        35                  40                  45

Ala Gln Leu Ile Gly Asp Asp Ile Val Arg Cys Ile Ala Leu Gly Pro
    50                  55                  60

Thr Glu Gly Leu Ala Arg Asn Glu Lys Val Thr Asn Tyr Asn His Pro
65                  70                  75                  80

Ile Glu Val Pro Val Gly Lys Asn Val Leu Gly Arg Met Phe Asn Val
                85                  90                  95

Leu Gly Lys Pro Ile Asp Gly Lys Glu Glu Leu Pro Lys Lys Pro Gln
            100                 105                 110

Leu Pro Ile His Arg Lys Pro Pro Ser Phe Asp Asp Gln Ser Asn Thr
        115                 120                 125

Leu Glu Ile Phe Glu Thr Gly Ile Lys Val Ile Asp Leu Leu Thr Pro
    130                 135                 140

Tyr Ala Arg Gly Gly Lys Ile Gly Leu Phe Gly Gly Ala Gly Val Gly
145                 150                 155                 160

Lys Thr Val Leu Val Gln Glu Leu Ile His Asn Ile Ala Lys Glu His
                165                 170                 175

Ser Gly Leu Ser Val Phe Ala Gly Val Gly Glu Arg Thr Arg Glu Gly
            180                 185                 190

Asn Asp Leu Tyr Tyr Glu Met Ile Gln Gly Gly Val Ile Asp Lys Thr
        195                 200                 205

Ala Leu Val Phe Gly Gln Met Asn Glu Pro Pro Gly Ala Arg Met Arg
    210                 215                 220

Val Ala Leu Thr Ala Leu Thr Met Ala Glu Tyr Phe Arg Asp His Asp
225                 230                 235                 240

Asn Gln Asp Val Leu Leu Phe Ile Asp Asn Ile Phe Arg Phe Thr Gln
                245                 250                 255

Ala Gly Ser Glu Val Ser Ala Leu Leu Gly Arg Met Pro Ser Ala Val
            260                 265                 270

Gly Tyr Gln Pro Thr Leu Ala Thr Glu Met Gly Gln Leu Gln Glu Arg
        275                 280                 285

Ile Ala Ser Thr Lys Thr Gly Ser Ile Thr Ser Val Gln Ala Ile Tyr
    290                 295                 300

Val Pro Ala Asp Asp Leu Thr Asp Pro Ala Pro Ala Thr Thr Phe Thr
305                 310                 315                 320

His Leu Asp Ala Lys Thr Val Leu Asp Arg Asn Ile Ala Ala Leu Gly
                325                 330                 335

Ile Phe Pro Ala Ile Asn Pro Leu Glu Ser Thr Ser Arg Leu Leu Asp
            340                 345                 350

Pro Asn Ile Val Gly Ile Asn His Tyr Lys Val Ala Leu Gly Val Gln
        355                 360                 365
```

```
                    -continued

Asn Ile Leu Gln Arg Phe Ala Glu Leu Gln Asp Ile Ile Ala Ile Leu
        370                 375                 380

Gly Ile Asp Glu Leu Ala Asp Glu Asp Lys Ile Ile Val Glu Arg Ala
385                 390                 395                 400

Arg Arg Ile Arg Asn Phe Leu Ser Gln Pro Phe Phe Val Ala Glu Lys
            405                 410                 415

Phe Ser Gly Ile Ala Gly Lys Tyr Val Pro Leu Ser Asp Thr Ile Gln
            420                 425                 430

Ser Phe Lys Glu Ile Leu Asp Gly Lys His Asp Asp Leu Pro Glu Gln
        435                 440                 445

Ala Phe Phe Val Gly Thr Ile Gln Glu Ala Val Glu Lys Ala Lys
        450                 455                 460

Arg Leu Lys Lys Ala Thr Val Glu Glu Lys
465                 470

<210> SEQ ID NO 3
<211> LENGTH: 22
<212> TYPE: DNA
<213> ORGANISM: Artificial Sequence
<220> FEATURE:
<223> OTHER INFORMATION: Synthetic Primer

<400> SEQUENCE: 3
aaaaaggaaa acattacata cg                                        22

<210> SEQ ID NO 4
<211> LENGTH: 17
<212> TYPE: DNA
<213> ORGANISM: Artificial Sequence
<220> FEATURE:
<223> OTHER INFORMATION: Synthetic Primer

<400> SEQUENCE: 4
tttctcctca acagtag                                              17
```